United States Patent [19]
Zanker

[11] 3,991,094
[45] Nov. 9, 1976

[54] MANUFACTURE OF ALKYL ISOCYANATES
[75] Inventor: Fritz Zanker, Worms, Germany
[73] Assignee: BASF Aktiengesellschaft, Ludwigshafen (Rhine), Germany
[22] Filed: Feb. 27, 1975
[21] Appl. No.: 553,499

[30] Foreign Application Priority Data
Mar. 11, 1974 Germany............................ 2411442

[52] U.S. Cl. ..................... 260/453 P; 260/453 PH
[51] Int. Cl.² ...................................... C07C 118/00
[58] Field of Search .................. 260/453 P, 453 PH

[56] References Cited
UNITED STATES PATENTS
3,388,145   6/1968   Merz.................................. 260/453
3,465,023   9/1969   Kamal................................ 260/453

Primary Examiner—Lewis Gotts
Assistant Examiner—Dolph H. Torrence
Attorney, Agent, or Firm—Johnston, Keil, Thompson & Shurtleff

[57] ABSTRACT

Aliphatic isocyanates are manufactured by thermal decomposition of aliphatic carbamic acid halides, an inert gas being passed in during the decomposition and being removed together with the hydrogen halide formed.

The isocyanates which may be manufactured by the process of the invention, particularly ethyl isocyanate, n-propyl isocyanate and isopropyl isocyanate, are valuable starting materials for the manufacture of plant protection agents, pesticides, dyes, synthetic resins, plastics, hydrophobic agents for textiles, detergents, bleaches and adhesives.

6 Claims, No Drawings

MANUFACTURE OF ALKYL ISOCYANATES

This application discloses and claims subject matter described in German patent application P 24 11 442.9, filed Mar. 11, 1974, which is incorporated herein by reference.

The invention relates to a process for the manufacture of aliphatic isocyanates by thermal decomposition of aliphatic carbamic acid halides, wherein an inert gas is passed in during the decomposition and removed together with the hydrogen halide formed.

The manufacture of isocyanates from carbamic acid chlorides using organic bases, such as tertiary amines or N,N-dialkylcarboxylic acid amides (German Published Application No. 1,593,554) in organic solvents is known. Isocyanates can also be obtained by using aqueous solutions or suspensions of inorganic bases, such as alkali metal hydroxides, alkaline earth metal hydroxides, alkali metal carbonates, alkaline earth metal carbonates or alkali metal bicarbonates (British Pat. No. 1,208,862). The above processes have the disadvantage that the isocyanates are produced in a medium in which they decompose easily. Thus it is known from Houben-Weyl, Methoden der organischen Chemie, Volume 8, page 136 (1952) that isocyanates dimerize in the presence of tertiary amines. Isocyanates are extremely unstable to aqueous alkali and a substantial degree of conversion to carbamates or carbamic acid occurs even if stoichiometric amounts of aqueous alkali are used. U.S. Pat. No. 3,465,023 states that a method of reacting polyamines and phosgene and, after completion of reaction, removing the hydrogen chloride formed from the reaction mixture by passing in an inert gas, such as nitrogen, has already been disclosed. Hydrogen chloride in the reaction mixture has an adverse effect on the end product, as stated in the above patent, and therefore has to be removed. It is pointed out that whilst the use of an inert gas assists the removal of the hydrogen chloride, it does not shift the reaction equilibrium sufficiently and therefore, in the case of the reaction of polyamines, a proportion of carbamic acid chloride always remains in the reaction mixture, decomposes on isolation of the isocyanate and therefore detracts from the yield and purity of the end product. The above U.S. patent teaches that satisfactory removal of hydrogen chloride, complete conversion of the carbamic acid chloride and hence good yield and high purity of the end product are only achievable by an alkaline wash of the reaction mixture.

A publication in Annalen der Chemie, 562, 75 – 109 (1949) describes the thermal decomposition of N-phenylcarbamic acid chloride, but points out that aliphatic isocyanates cannot be obtained by thermal decomposition of the corresponding carbamic acid chlorides, in contrast to the decomposition of aromatic carbamic acid chlorides. Entirely in agreement with the above publications, the isocyanates can only be isolated by binding the hydrogen chloride by chemical reagents such as calcium oxide; however, even in that case sidereactions, such as the formation of polymeric isocyanates, at times come into play (page 78). The higher aliphatic isocyanates can be prepared by reaction of hydrochlorides of aliphatic amines with phosgene at elevated temperatures in a solvent which is inert under the reaction conditions. As regards the use of inert gases, the publication shows that they are only used to remove the residual phosgene and hydrogen chloride after completion of the reaction, for which purpose the inert gases are not passed through the reaction mixture but always over the surface of the mixture (page 100 and page 101). The publication shows (page 81) that in the case of the lowest members of the aliphatic series the isocyanates are not obtainable by this method; with methylamine, ethylamine and propylamine, the carbamic acid chlorides are obtained as the end product.

German Pat. No. 1,193,034 refers to the publication in Annalen (loc.cit.) and states that alkyl isocyanates cannot be manufactured by thermal decomposition of carbamic acid chlorides in the above manner; instead, this patent proposes that the decomposition be carried out with simultaneous removal of the hydrogen chloride through a reflux condenser and of the isocyanate through a column, both from the same reaction chamber. Houben-Weyl (loc.cit., page 121) also states that the process of phosgenation of amine hydrochlorides described in Annalen (loc.cit.) is unsuitable for the manufacture of isocyanates of the lowest members of the aliphatic series.

It is an object of the present invention to provide a new process for the simpler and more economical manufacture of isocyanates, in some cases in better yield and higher purity.

We have found that aliphatic isocyanates of the formula

where R is an aliphatic radical of 1 to 10 carbon atoms, are obtained advantageously by thermal decomposition of aliphatic carbamic acid halides of the formula

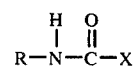

where R has the above meaning and X is halogen, in the presence of inert, organic solvents, by passing a gas which is inert under the reaction conditions through the reaction mixture during the reaction and removing it from the mixture, together with the hydrogen halide formed.

Where isopropylcarbamic acid chloride is used, the reaction can be represented by the equation:

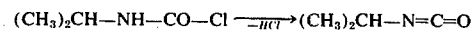

Compared to conventional processes, the process of the invention gives isocyanates more simply and more economically and in some cases in better yield and higher purity. Special auxiliaries, for example alkalis and, in particular, expensive organic bases, are not used. Further, whereas all processes of phosgenation of amine hydrochlorides require the introduction or presence of phosgene also during the conversion of the carbamic acid chlorides, formed as intermediates, to isocyanates, such is not the case in the novel process. Compared to the process described in German Pat. No. 1,193,034 it is now possible to avoid simultaneous distilling and separating off of hydrogen chloride and isocyanate through separate distillation apparatuses — which was difficult to control in operation — and this represents an advantage, particularly in industrial operation, in respect of monitoring, control, reduced number of operatives required and corresponding reduction in control equipment. Expensive columns which permit precise separation are also not required. These advantageous findings are surprising, since the state of the art would have suggested substantial re-formation of the starting materials from the isocyanate formed and the hydrogen halide. In view of the low boiling points of the end products of the invention and the absence of phosgene, it would have been expected that prolonged agitation of the reaction mixture by the inert gas passed into it would transfer an increased proportion of isocyanate into the gas space above the surface of the batch undergoing decomposition and would lead to increased re-formation of carbamic acid halide and a poorer yield of end product, since more intimate mixing of the isocyanate formed and the hydrogen halide, by the inert gas, affords greater opportunity of reaction between the molecule of these compounds.

It is a further advantage of the process of the invention that a surprisingly high concentration of carbamic acid halide II in the solvent can be used without significant polymerization of the isocyanate formed. As a result of the high concentration, the energy costs for the thermal decomposition and the subsequent separation of isocyanate and solvent by distillation are relatively low. The substantial additional costs of working up, and the reduction in yield, which necessarily arise in the process using added bases, do not apply here.

Preferred starting materials II and, correspondingly, preferred end products I are those in which R is alkyl of 1 to 10 carbon atoms, preferably of 1 to 4 carbon atoms and especially of 2 or 3 carbon atoms, alkenyl of 2 to 6 carbon atoms or alkynyl of 2 to 6 carbon atoms and X is bromine or preferably chlorine. The above radicals can in addition be substituted by groups and/or atoms which are inert under the reaction conditions, e.g. alkyl of 1 to 5 carbon atoms, alkoxy of 1 to 5 carbon atoms or chlorine.

Examples of starting materials II are methyl-, ethyl-, n-propyl-, i-propyl-, n-butyl-, i-butyl-, sec.-butyl-, t-butyl-, 2-methylbutyl-(1)-, 3-methylbutyl-(1)-, 2-methylbutyl-(2)-, 3-methylbutyl-(2), pentyl-(1)-, pentyl-(2)-, pentyl-(3)-, neo-pentyl-, n-hexyl-, n-octyl-, allyl-, 3,3-dimethyl-allyl-(3)-, 3-methyl-3-ethyl-allyl-(3)-, butin-(1)-yl-(3)-, 3-methyl-butin-(1)-yl-(3)-, 3-methyl-pentin-(1)-yl-(3)-, 2-methoxyethyl-, 2-ethoxyethyl-, 3-methoxypropyl-, 3-ethoxypropyl-, 1-methoxy-butyl-(2)-, 1-n-propoxy-propyl-(2)-, methoxy-t-butyl- and ethoxy-t-butyl-carbamic acid chloride and corresponding carbamic acid bromides. Ethylcarbamic acid chloride, n-propylcarbamic acid chloride and isopropylcarbamic acid chloride are preferred.

The decomposition is generally carried out at from +30° to 180° C, preferably from 45° to 140° C, and especially from 70° to 115° C, advantageously under reflux at the boiling point of the mixture of starting material II and solvent which is undergoing decomposition, under atmospheric or superatmospheric pressure, continuously or batchwise. The organic solvents used are inert under the reaction conditions and are, advantageously, good solvents for the starting material II but non-solvents or poor solvents for the hydrogen halide. It is expedient to use solvents boiling above 60° C. Examples of possible solvents are aromatic hydrocarbons, for example benzene, toluene, ethylbenzene, o-, m- and p-xylene, isopropylbenzene, o-, m- and p-cymene and methylnaphthalene; halohydrocarbons, in particular chlorohydrocarbons, e.g. tetrachloroethylene, tetrachloroethane, carbon tetrachloride, trichloroethane, trichloroethylene, pentachloroethane, cis-dichloroethylene, o-, m- and p-difluorobenzene, 1,2-dichloroethane, 1,1-dichloroethane, n-propyl chloride, 1,2-cis-dichloroethylene, n-butyl chloride, 2-, tert.- and iso-butyl chloride, chlorobenzene, bromobenzene, iodobenzene, o-, p- and m-dichlorobenzene, fluorobenzene, o-, p- and m-dibromobenzene, o-, m- and p-chlorotoluene, 1,2,4-trichlorobenzene, 1,10-dibromodecane, amyl chloride, cyclohexyl chloride, 1,3-dichloropropane, 1,4-dichlorobutane, isopropyl bromide, n-propyl bromide, butyl bromide, ethyl iodide, propyl iodide, chloronaphthalene, dichloronaphthalene and 1,4-dibromobutane; ethers, e.g. n-butyl ethyl ether, ethyl propyl ether, methyl tert.-butyl ether, di-n-butyl ether, di-iso-amyl ether, di-iso-propyl ether, anisole, phenetole, cyclohexyl methyl ether, tetrahydrofuran, thioanisole and $\beta,\beta'$-dichlorodiethyl ether; ketones, such as methyl ethyl ketone, diethyl ketone, acetophenone and cyclohexanone; esters such as methyl acetate, methyl benzoate, methyl propionate, butyl acetate, ethyl formate, ethyl acetate, methyl phthalate and phenyl acetate; nitrohydrocarbons, such as nitromethane, nitroethane, nitrobenzene, o-, m- and p-chloronitrobenzene and o-nitrotoluene; nitriles, such as acetonitrile, benzonitrile and m-chlorobenzonitrile; aliphatic or cycloaliphatic hydrocarbons, for example decane, dodecane, hexane, heptane, nonane, gasoline fractions within the above boiling point range, cyclohexane, methylcyclohexane, cyclooctane, cyclododecane, petroleum ether, decalin, ligroin, 2,2,4-trimethylpentane, 2,2,3-trimethylpentane, 2,3,3-trimethylpentane and octane, and mixtures of the above. Suitable amounts of solvent to use are from 50 to 1,500% by weight, preferably from 80 to 900% by weight, based on starting material II.

Suitable gases inert under the reaction conditions which may be used are rare gases such as xenon, argon, neon and helium, alkanes such as methane, ethane, propane, 2,2-dimethylpropane, butane, pentane and isobutane, gaseous halohydrocarbons such as tetrafluoromethane, dichloromethane, chloromethane, bromomethane, hexafluoroethane, chloroethane and fluoroethane, gaseous organic compounds of inorganic elements, such as tetramethylsilane, ethers such as dimethyl ether and methyl ethyl ether and, preferably, nitrogen, oxygen, air and/or dioxide, and mixtures of the above.

In a preferred embodiment of the process, at least 80, preferably from 150 to 10,000, and in particular from 200 to 8,000 parts by volume of inert gas are used per part by weight of starting material II; under these conditions the amount of solvent is advantageously from 50 to 1,500% by weight, preferably 80 to 900% by weight, based on the weight of starting material II. The preferred flow rate of the inert gas through the mixture undergoing decomposition is from 10 to 300, preferably from 30 to 240, parts by volume per hour per part by weight of starting material II. Particularly under the above preferred reaction conditions, there is no significant reformation of starting material II from isocyanate I and the hydrogen halide eliminated, but there is also no significant entrainment of starting material or end product by the gas mixture leaving the reflux condenser. A further particular advantage of the process of the invention is that the decomposition and removal of the hydrogen halide can be accelerated by using a higher flow rate of inert gas, so that a decomposition time of the order of magnitude desired in industrial operation is achievable. It is possible to decompose the starting material and only to pass in the inert gas during the decomposition, e.g. from 0.5 to 20 hours after the start of the decomposition of the starting material mixed with the solvent; however, it is more advantageous to introduce the inert gas from the start, i.e. from the beginning of the decomposition. If the inert gas is recycled, it is preferably freed from hydrogen halide, e.g. by absorbing the latter in water to form hydrochloric acid, and dried, before re-entering the decomposition mixture.

The reaction may be carried out as follows: a mixture of starting material II and solvent is kept under reflux at the decomposition temperaure for from 1 to 20 hours, whilst being mixed thoroughly and whilst passing the inert gas through it. It is advisable to ensure efficient reflux condensation during the reaction. The inert gas can be passed through the reaction mixture intermittently or, preferably, continuously. The inert gas and the hydrogen halide formed are discharged as off-gas through the reflux condenser. In general, the equipment used comprises columns with reflux fittings, as a rule distillation apparatuses with reflux condensers, and is set to give total reflux of the organic components of the reaction mixture. The temperature of the reflux condenser is as a rule below the boiling point of end product I, preferably at from −30° to +30° C. If appropriate, several condensers, or condensers arranged in series, may be used. Isocyanates, carbamic acid halide and/or solvent which may have been entrained with the inert gas and with the hydrogen chloride eliminated, and may have passed through the condenser in proportion to the vapor pressures, can be scrubbed out with recycled solvent and subjected to renewed thermal decomposition in this solvent after addition of carbamic acid chloride. The end product is then isolated from the decomposition mixture by conventional methods, e.g. by fractional distillation. The solvent isolated is usually so pure that it can be used direct for several, e.g. from 4 to 6, further decomposition reactions. Thereafter, the solvent can be purified by distillation or by washing with water and then removing the residual from the solvent, e.g. by azeotropic distillation.

The process according to the invention can, if appropriate, also be carried out under the conditions of the process described in German Published Application p 24 11 441.8 in which, in a first stage, the starting material II is decomposed at a temperature at least 25° C above its boiling point, in the presence of a solvent boiling at or above this temperature, whilst passing an inert gas through the mixture and removing the hydrogen halide formed, and then, in a second stage, isolating the resulting isocyanate I from the decomposition mixture by distillation.

The isocyanates which may be manufactured by the process of the invention, preferably ethyl isocyanate, n-propyl isocyanate and isopropyl isocyanate, are valuable starting materials for the manufacture of plant protection agents, pesticides, dyes, synthetic resins and plastics, hydrophobic agents for textiles, detergents, bleaches and adhesives. Their conversion to urethanes, for example for use as foams or high molecular weight coatings of great flexibility, or to ureas, is of particular importance. For details of their use, reference may be made to the above publications and to Ullmanns Encyklopadie der technischen Chemie, Volume 9, pages 11, 12 and 404, and Volume 17, page 204.

In the examples which follow, parts are by weight and bear the same relation to parts by volume as that of the kilogram to the liter.

EXAMPLE 1

A solution of 1,114 parts of isopropylcarbamic acid chloride in 1,134 parts of toluene is heated for 15 hours under reflux in a stirred vessel equipped with an inlet tube carrying a (glass) frit, and a reflux condenser, in which the cooling medium is at from +10° to −30° C. At the same time, 60,000 parts by volume of dry nitrogen per hour are introduced via the inlet tube and passed through the solution. The nitrogen and the hydrogen chloride eliminated escape through the reflux condenser. The temperature in the vessel rises from 56° to 86° C during the reaction. At the end of the reaction, the solution is free from carbamic acid chloride, and is distilled. Yield 717 parts of isopropyl isocyanate (corresponding to 92% of theory, based on isopropylcarbamic acid chloride used) boiling at 74° C.

EXAMPLE 2

A solution of 970 parts of isopropylcarbamic acid chloride in 1,020 parts of chlorobenzene is inroduced into an apparatus analogous to that of Example 1 and is refluxed for 9 hours — during which the reaction temperature rises from 77° to 88° C — whilst passing 120,000 parts by volume of dry nitrogen per hour through the mixture. The subsequent distillation gives 630 parts of isopropyl isocyanate free from carbamic acid chloride (corresponding to 93% of theory, based on isopropylcarbamic acid chloride used), boiling at from 73.5° to 74.5° C.

EXAMPLE 3

Analogously to Example 1, 150,000 parts by volume of dry nitrogen per hour are passed for 7 hours through a solution, boiling under reflux, of 1,055 parts of isopropylcarbamic acid chloride in 1,106 parts of xylene. Distillation gives 700 parts of chloride-free isopropyl isocyanate (corresponding to 94.8% of theory, based on isopropylcarbamic acid chloride used) boiling at 74° C.

EXAMPLE 4

Analogously to Example 1, 75,000 parts by volume of carbon dioxide per hour are passed for 11 hours through a mixture of 550 parts of isopropylcarbamic acid chloride and 550 parts of toluene under reflux. During this time, the decomposition temperature rises from 72° to 84° C. Finally, the reaction mixture is distilled. Yield of pure isopropyl isocyanate 356 parts (corresponding to 92.3% of theory, based on isopropylcarbamic acid chloride used) boiling at 74° C.

EXAMPLE 5

160 Parts of ethylcarbamic acid chloride are dissolved in 300 parts of methylcyclohexane. The mixture is refluxed for 7 hours, analogously to Example 1, whilst passing 25,000 parts by volume of nitrogen per hour through it. The reaction temperature rises from 75° to 80° C. Distillation gives 97.5 parts of pure ethyl isocyanate (corresponding to 92.3% of theory, based on ethylcarbamic acid chloride used) boiling at from 59.5° to 60.5° C.

EXAMPLE 6

Analogously to Example 1, 25,000 parts by volume of nitrogen per hour are passed for 7 hours through a refluxing mixture of 214 parts of isopropylcarbamic acid chloride and 150 parts of o-dichlorobenzene. During this time the temperature rises from 86° to 90° C. Distillation of the reaction mixture gives 139 parts of pure isopropyl isocyanate (corresponding to 92.8% of theory, based on isopropylcarbamic acid chloride used) boiling at from 73° to 74° C.

EXAMPLE 7

Analogously to Example 1, 5,000 parts by volume of propane per hour are passed for 8 hours through a refluxing solution of 105 parts of n-propylcarbamic acid chloride in 595 parts of xylene. During this time the reaction temperature rises from 106° to 115° C. The distillation of the mixture gives 70 parts of n-propyl isocyanate (corresponding to a yield of 95% of theory, based on n-propylcarbamic acid chloride used) boiling at 88° C.

EXAMPLE 8

The apparatus used is as in Example 1, with two reflux condensers. 10,000 parts by volume of air per hour are passed for 10 hours into a solution of 210 parts of isopropylcabamic acid chloride in 480 parts of n-butyl acetate. During the first hour, the mixture is refluxed, and the reaction temperature rises from 79° to 102° C. The mixture is then kept at 102° C for two hours, during which boiling subsides. For the remaining seven hours, the mixture is again boiled under reflux, during which time the temperature rises to 107° C. Distillation of the reaction mixture gives 138 parts of pure isopropyl isocyanate (corresponding to 93.8% of theory, based on isopropylcarbamic acid chloride used) boiling at from 73° to 74° C.

I claim:
1. A process for the manufacture of alkyl isocyanates of the formula

$$R - N = C = O \qquad I$$

where R is ethyl, n-propyl or isopropyl, by thermal decomposition of alkyl carbamic acid halides of the formula $$R-\underset{H}{\overset{}{N}}-\underset{}{\overset{O}{C}}-X \qquad II$$

where R has the above meaning and X is halogen, in 50 to 1500 percent by weight, based on said carbamic acid halide II, of an inert, organic solvent, wherein 150 to 10,000 parts by volume, based on said carbamic acid halide II, of a gas which is inert under the reaction conditions is pased through the reaction mixture during the decomposition and is removed from the mixture, together with the hydrogen halide formed, said organic solvent boiling above 60° C., being inert under the reaction conditions, and being a non-solvent or poor solvent for the hydrogen halide.

2. A process as claimed in claim 1, wherein the decomposition is carried out at from 30° to 180° C.

3. A process as claimed in claim 1, wherein the decomposition is carried out at from 45° to 140° C.

4. A process as claimed in claim 1, wherein the decomposition is carried out at from 70° to 115° C.

5. A process as claimed in claim 1, wherein the decomposition is carried out with at least 8 parts by volume of inert gas per part of carbamic acid halide II.

6. A process as claimed in claim 1, wherein the flow rate of the inert gas passed through the decomposition mixture is from 10 to 300 parts by volume per hour per part of carbamic acid halide II.

* * * * *

UNITED STATES PATENT AND TRADEMARK OFFICE
CERTIFICATE OF CORRECTION

PATENT NO. : 3,991,094
DATED : November 9, 1976
INVENTOR(S) : Fritz Zanker

It is certified that error appears in the above-identified patent and that said Letters Patent are hereby corrected as shown below:

In Column 5, Line 30, delete " ... Isocyanates, carbamic ... " and substitute -- ... Isocyanate, carbamic ... --

In Column 6, Line 25, delete " ... is inroduced ... " and substitute -- ... is introduced ... --

In Column 8, Line 20, delete " ... is pased through ... " and substitute -- ... is passed through ... --

Signed and Sealed this

Seventh Day of June 1977

[SEAL]

Attest:

RUTH C. MASON
*Attesting Officer*

C. MARSHALL DANN
*Commissioner of Patents and Trademarks*